March 17, 1964 J. McINTYRE Plant Pat. 2,377
MAPLE TREE
Filed April 2, 1963
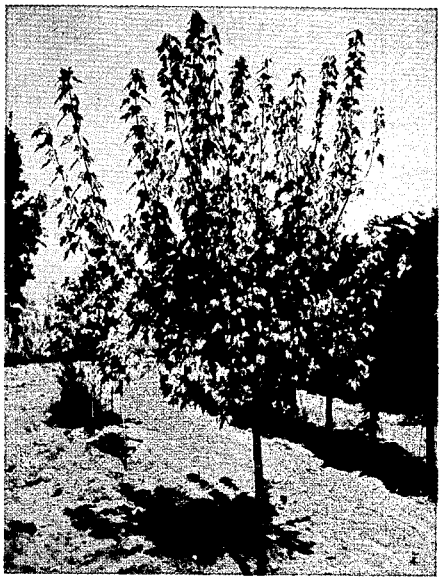
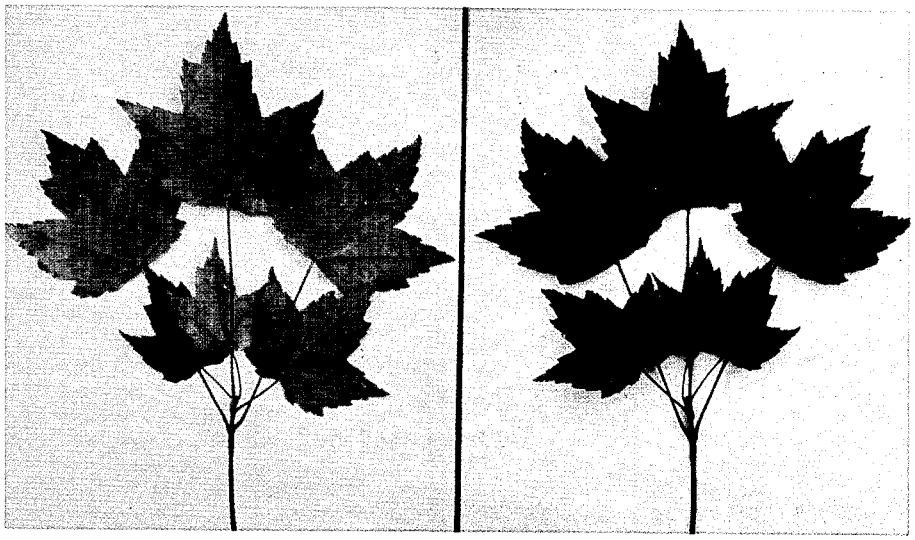
Inventor.
John McIntyre
By: Robert Robb
Attorneys.

United States Patent Office

Plant Pat. 2,377
Patented Mar. 17, 1964

2,377
MAPLE TREE

John McIntyre, Gresham, Oreg., assignor to Wayne E. McGill, doing business as A. McGill & Son, Fairview, Oreg.

Filed Apr. 2, 1963, Ser. No. 270,127
1 Claim. (Cl. Plt.—51)

The present invention relates to a new and distinct variety of maple tree, which was originated by me as a selected seedling derived from my planting of seeds of an unnamed and unpatented variety of *Acer rubrum,* as grown under my direction and control in the nursery of my assignee at Fairview, Oregon.

In originating this new variety of maple tree, I was growing a block of seedlings in the nursery referred to above, from which this particular variety was chosen by me because of its brilliant scarlet autumn coloring, combined with an unusually small leaf size. The selected plant was removed from the seedling block and replanted in a test block where I could keep it under close observation. Continued observations and tests of the new seedling, as well as progeny thereof derived from buddings performed by me in the nursery aforementioned, conclusively established that the new seedling was definitely distinguished from the regular *Acer rubrum,* as well as from all other varieties of which I am aware, as evidenced by the following unique combination of characteristics which are outstanding therein:

(1) A habit of bearing leaves of smaller size than those of the average seedlings of *Acer rubrum* and *Acer rubrum schlesingeri,* with the leaves being borne in greater profusion;

(2) An extremely early coloring of the foliage, ranging from two to three weeks earlier than the variety *Acer rubrum schlesingeri,* combined with the ability to hold the colored leaves for an unusually long period of time; and (3) Brilliant scarlet autumn coloring of the leaves.

The accompanying drawing shows a typical specimen young tree of the new maple variety as grown in the test block of my assignee's nursery at Fairview, Oregon, and also shows typical specimen leaves on a somewhat enlarged scale, depicting both the under and upper surfaces of the leaves, all as illustrated in color as nearly true as it is reasonably possible to make the same in an illustration of this character.

The following is a detailed description of my new maple tree variety, with color terminology in accordance with the Exotica Horticultural Color Guide, published by Roehrs Company of Rutherford, New Jersey, except where general color terms of ordinary dictionary significance are obvious:

Parentage: An unnamed seedling of *Acer rubrum.*
Propagation: Holds its distinguishing characteristics through succeeding propagations by budding.

Locality where grown and observed: Fairview, Oregon.
Tree: Medium tall; ovate spreading; hardy.
*Trunk.*—Moderately stout; smooth.
*Branches.*—Slender; smooth. Color—Brown, Color No. 14, as distinguished from the grayish brown color of *Acer rubrum.*
*Lenticels.*—Fewer than *Acer rubrum.*
Foliage:
*Leaves.*—Profuse quantity; medium thickness. Size: length—about 8 cm.; width—about 9 cm. Shape—from 3 to 5 lobed. Color: upper surface—green (a blend of Grass Green, Color No. 73 and Paris Green, Color No. 74), turning to Scarlet, Color No. 25 in the autumn; under surface—glaucous green (a blend of Aquamarine, Color No. 64 and Seafoam, Color No. 71), with a bluish gray bloom slightly lighter than Flax Blue, Color No. 58. Margin—crenate-serrate. Petiole—medium length (from 3.5 cm. to 4 cm.). Glands—none. Stipules—none.
Flower buds:
*Size.*—About 4 or 5 mm. in diameter.
*Shape.*—Oval.
*Color of sepals.*—Light greenish yellow (a blend of Chartreuse, Color No. 78 and Citron, Color No. 79), over basal portion, with carmine red, somewhat darker than Carmine, Color No. 31, at tip.
Flowers:
*Date of first bloom.*—About March 1st.
*Date of full bloom.*—About March 7th.
*Quantity.*—Normal.
*Size.*—Small.
*Color.*—Carmine red, somewhat darker than Carmine, Color No. 31, with light greenish yellow (a blend of Chartreuse, Color No. 78 and Citron, Color No. 79) at base.
Petals:
*Number.*—5.
*Shape.*—Oblong.
*Size.*—Length—about 1.5 mm. Width—about 0.5 mm.
General observations: Pedicels are approximately 5 mm. long at anthesis: staminate and bisexual on same tree andromonoecious).

I claim:

A new and distinct variety of maple tree, substantially as herein shown and described, characterized particularly as to novelty by the unique combination of a habit of bearing leaves of smaller size than those of the average seedlings of *Acer rubrum* and *Acer rubrum schlesingeri,* with the leaves being borne in greater profusion, an extremely early coloring of the foliage ranging from two to three weeks earlier than *Acer rubrum schlesingeri,* combined with the ability to hold the colored leaves for an unusually long period of time, and a distinctive and attractive brilliant scarlet autumn coloring of the foliage.

No references cited.